US008790255B2

(12) United States Patent
Behar

(10) Patent No.: US 8,790,255 B2
(45) Date of Patent: Jul. 29, 2014

(54) COMPUTER INTERFACES INCLUDING PHYSIOLOGICALLY GUIDED AVATARS

(75) Inventor: Andrew Behar, Ojai, CA (US)

(73) Assignee: adidas AG, Herzogenaurach (DE)

( * ) Notice: Subject to any disclaimer, the term of this patent is extended or adjusted under 35 U.S.C. 154(b) by 0 days.

(21) Appl. No.: 13/239,651

(22) Filed: Sep. 22, 2011

(65) Prior Publication Data

US 2012/0071771 A1 Mar. 22, 2012

Related U.S. Application Data

(63) Continuation of application No. 11/492,484, filed on Jul. 24, 2006, now Pat. No. 8,033,996.

(60) Provisional application No. 60/702,779, filed on Jul. 26, 2005.

(51) Int. Cl.
*A61B 5/02* (2006.01)
*A61B 5/08* (2006.01)
*A61B 5/113* (2006.01)
*A61B 5/00* (2006.01)
*G06T 13/40* (2011.01)
*G06F 19/00* (2011.01)
*A61B 5/0205* (2006.01)
*A61B 5/11* (2006.01)
*G06T 13/00* (2011.01)

(52) U.S. Cl.
CPC ....... *G06T 13/40* (2013.01); *G06T 2207/30004* (2013.01); *G06T 2207/30104* (2013.01); *G06T 2210/41* (2013.01); *G06T 2215/16* (2013.01); *G06F 196/34* (2013.01); *G06F 19/3418* (2013.01); *G06F 19/3437* (2013.01); *A61B 5/08* (2013.01); *A61B 5/0205* (2013.01); *A61B 5/0022* (2013.01); *A61B 5/6801* (2013.01); *A61B 5/1118* (2013.01)

USPC ........... 600/300; 600/301; 600/481; 600/529; 600/534; 345/473; 345/467; 715/706; 482/8

(58) Field of Classification Search
USPC ................. 600/300–301, 363–365, 372–374, 600/377–379, 382–384, 386–394, 481, 485, 600/500–503, 508, 515–519, 529–531, 600/544–547, 549, 587–595
See application file for complete search history.

(56) References Cited

U.S. PATENT DOCUMENTS 3,534,727 A 10/1970 Roman
3,731,184 A 5/1973 Goldberg et al.
(Continued)

FOREIGN PATENT DOCUMENTS

DE 4214263 11/1993
EP 0262778 4/1988
(Continued)

OTHER PUBLICATIONS

6th Portuguese Conference on Biomedical Engineering, "BioEng' 2001 Conference Papers", (Jun. 2001) 6 pages.

(Continued)

*Primary Examiner* — Gary Jackson
*Assistant Examiner* — Marie Archer
(74) *Attorney, Agent, or Firm* — Sterne, Kessler, Goldstein & Fox P.L.L.C.

(57) ABSTRACT

This invention provides user interfaces that more intuitively display physiological data obtained from physiological monitoring of one or more subjects. Specifically, the user interfaces of this invention create and display one or more avatars having behaviors guided by physiological monitoring data. The monitoring data is preferably obtained when the subject is performing normal tasks without substantial restraint. This invention provides a range of implementations that accommodate user having varying processing and graphics capabilities, e.g., from handheld electronic devices to ordinary PC-type computers and to systems with enhanced graphics capabilities.

25 Claims, 5 Drawing Sheets

(56) References Cited

U.S. PATENT DOCUMENTS

| | | |
|---|---|---|
| 3,874,368 A | 4/1975 | Asrican |
| 3,926,177 A | 12/1975 | Hardway, Jr. et al. |
| 4,016,868 A | 4/1977 | Allison |
| 4,033,332 A | 7/1977 | Hardway, Jr. et al. |
| 4,102,331 A | 7/1978 | Grayzel et al. |
| 4,267,845 A | 5/1981 | Robertson, Jr. et al. |
| 4,289,142 A | 9/1981 | Kearns |
| 4,306,567 A | 12/1981 | Krasner |
| 4,308,872 A | 1/1982 | Watson et al. |
| 4,373,534 A | 2/1983 | Watson |
| 4,387,722 A | 6/1983 | Kearns |
| 4,433,693 A | 2/1984 | Hochstein |
| 4,446,872 A | 5/1984 | Marsoner et al. |
| 4,452,252 A | 6/1984 | Sackner |
| 4,456,015 A | 6/1984 | Sackner |
| 4,463,764 A | 8/1984 | Anderson et al. |
| 4,494,553 A | 1/1985 | Sciarra et al. |
| 4,545,376 A | 10/1985 | Beiter |
| 4,546,777 A | 10/1985 | Groch et al. |
| 4,548,204 A | 10/1985 | Groch et al. |
| 4,549,552 A | 10/1985 | Groch et al. |
| 4,572,197 A | 2/1986 | Moore et al. |
| 4,580,572 A | 4/1986 | Granek et al. |
| 4,585,718 A | 4/1986 | Uedaira et al. |
| 4,648,407 A | 3/1987 | Sackner |
| 4,672,975 A | 6/1987 | Sirota |
| 4,753,088 A | 6/1988 | Harrison et al. |
| 4,777,962 A | 10/1988 | Watson et al. |
| 4,796,639 A | 1/1989 | Snow et al. |
| 4,800,495 A | 1/1989 | Smith |
| 4,807,640 A | 2/1989 | Watson et al. |
| 4,815,473 A | 3/1989 | Watson et al. |
| 4,817,625 A | 4/1989 | Miles |
| 4,819,752 A | 4/1989 | Zelin |
| 4,834,109 A | 5/1989 | Watson |
| 4,860,766 A | 8/1989 | Sackner |
| 4,863,265 A | 9/1989 | Flower et al. |
| 4,867,571 A | 9/1989 | Frick et al. |
| 4,889,131 A | 12/1989 | Salem et al. |
| 4,909,260 A | 3/1990 | Salem et al. |
| 4,911,167 A | 3/1990 | Corenman et al. |
| 4,920,969 A | 5/1990 | Suzuki et al. |
| 4,928,692 A | 5/1990 | Goodman et al. |
| 4,934,372 A | 6/1990 | Corenman et al. |
| 4,955,379 A | 9/1990 | Hall |
| 4,960,118 A | 10/1990 | Pennock |
| 4,966,155 A | 10/1990 | Jackson |
| 4,972,842 A | 11/1990 | Korten et al. |
| 4,981,139 A | 1/1991 | Pfohl |
| 4,986,277 A | 1/1991 | Sackner |
| 5,007,427 A | 4/1991 | Suzuki et al. |
| 5,025,791 A | 6/1991 | Niwa |
| 5,036,857 A | 8/1991 | Semmlow et al. |
| 5,040,540 A | 8/1991 | Sackner |
| 5,074,129 A | 12/1991 | Matthew |
| 5,076,801 A | 12/1991 | Schroll |
| 5,099,841 A | 3/1992 | Heinonen et al. |
| 5,099,855 A | 3/1992 | Yount |
| 5,111,817 A | 5/1992 | Clark et al. |
| 5,131,399 A | 7/1992 | Sciarra |
| 5,143,089 A | 9/1992 | Alt |
| 5,159,935 A | 11/1992 | Sackner et al. |
| 5,173,151 A | 12/1992 | Namose |
| 5,178,151 A | 1/1993 | Sackner |
| 5,224,479 A | 7/1993 | Sekine |
| 5,241,300 A | 8/1993 | Buschmann |
| 5,271,551 A | 12/1993 | Roepke |
| 5,295,490 A | 3/1994 | Dodakian |
| 5,299,120 A | 3/1994 | Kaestle |
| 5,301,678 A | 4/1994 | Watson et al. |
| 5,307,678 A | 5/1994 | Cost |
| 5,329,932 A | 7/1994 | Yount |
| 5,333,106 A | 7/1994 | Lanpher et al. |
| 5,348,008 A | 9/1994 | Bornn et al. |
| 5,353,793 A | 10/1994 | Bornn |
| 5,416,961 A | 5/1995 | Vinay |
| 5,447,164 A | 9/1995 | Shaya et al. |
| RE35,122 E | 12/1995 | Corenman et al. |
| 5,520,192 A | 5/1996 | Kitney et al. |
| 5,533,511 A | 7/1996 | Kaspari et al. |
| 5,535,738 A | 7/1996 | Estes et al. |
| 5,544,661 A | 8/1996 | Davis et al. |
| 5,564,429 A | 10/1996 | Bornn et al. |
| 5,577,510 A | 11/1996 | Chittum et al. |
| 5,582,337 A | 12/1996 | McPherson et al. |
| 5,584,295 A | 12/1996 | Muller et al. |
| 5,588,425 A | 12/1996 | Sackner et al. |
| 5,601,088 A | 2/1997 | Swanson et al. |
| 5,611,085 A | 3/1997 | Rasmussen |
| 5,617,847 A | 4/1997 | Howe |
| 5,694,939 A | 12/1997 | Cowings |
| 5,718,234 A | 2/1998 | Warden et al. |
| 5,719,950 A | 2/1998 | Osten et al. |
| 5,720,709 A | 2/1998 | Schnall |
| 5,724,025 A | 3/1998 | Tavori |
| 5,749,365 A | 5/1998 | Magill |
| 5,820,567 A | 10/1998 | Mackie |
| 5,825,293 A | 10/1998 | Ahmed et al. |
| 5,848,027 A | 12/1998 | Dotter |
| 5,882,307 A | 3/1999 | Wright et al. |
| 5,899,855 A | 5/1999 | Brown |
| 5,913,830 A | 6/1999 | Miles |
| 5,921,920 A | 7/1999 | Marshall et al. |
| 5,937,854 A | 8/1999 | Stenzler |
| 5,989,193 A | 11/1999 | Sullivan |
| 5,991,922 A | 11/1999 | Banks |
| 6,002,952 A | 12/1999 | Diab et al. |
| 6,013,007 A * | 1/2000 | Root et al. .................. 482/8 |
| 6,015,388 A | 1/2000 | Sackner et al. |
| 6,018,677 A | 1/2000 | Vidrine et al. |
| 6,032,119 A * | 2/2000 | Brown et al. .................. 705/2 |
| 6,035,154 A | 3/2000 | Takahata et al. |
| 6,047,203 A | 4/2000 | Sackner et al. |
| 6,066,093 A | 5/2000 | Kelly et al. |
| 6,067,462 A | 5/2000 | Diab et al. |
| 6,068,568 A | 5/2000 | Kozakura et al. |
| 6,070,098 A | 5/2000 | Moore-Ede et al. |
| 6,102,856 A * | 8/2000 | Groff et al. .................. 600/301 |
| 6,120,441 A | 9/2000 | Griebel |
| 6,142,953 A | 11/2000 | Burton et al. |
| 6,145,551 A | 11/2000 | Jayaraman et al. |
| 6,179,786 B1 | 1/2001 | Young |
| 6,198,394 B1 | 3/2001 | Jacobsen et al. |
| 6,222,547 B1 * | 4/2001 | Schwuttke et al. .......... 345/419 |
| 6,223,072 B1 | 4/2001 | Mika et al. |
| 6,238,338 B1 * | 5/2001 | DeLuca et al. .............. 600/300 |
| 6,254,551 B1 | 7/2001 | Varis |
| 6,261,238 B1 | 7/2001 | Gavriely |
| 6,273,859 B1 | 8/2001 | Remmers et al. |
| 6,287,264 B1 | 9/2001 | Hoffman |
| 6,302,844 B1 | 10/2001 | Walker et al. |
| 6,306,088 B1 | 10/2001 | Krausman et al. |
| 6,341,504 B1 | 1/2002 | Istook |
| 6,361,501 B1 | 3/2002 | Amano et al. |
| 6,381,482 B1 | 4/2002 | Jayaraman et al. |
| 6,413,225 B1 | 7/2002 | Sackner et al. |
| 6,419,636 B1 | 7/2002 | Young et al. |
| 6,436,057 B1 | 8/2002 | Goldsmith |
| 6,443,890 B1 | 9/2002 | Schulze et al. |
| 6,449,504 B1 | 9/2002 | Conley et al. |
| 6,454,719 B1 | 9/2002 | Greenhut |
| 6,461,307 B1 | 10/2002 | Kristbjarnarson et al. |
| 6,463,385 B1 | 10/2002 | Fry |
| 6,478,736 B1 | 11/2002 | Mault |
| 6,483,929 B1 | 11/2002 | Murakami et al. |
| 6,485,431 B1 | 11/2002 | Campbell |
| 6,506,153 B1 | 1/2003 | Littek et al. |
| 6,511,424 B1 | 1/2003 | Moore-Ede et al. |
| 6,513,532 B2 | 2/2003 | Mault et al. |
| 6,551,252 B2 | 4/2003 | Sackner et al. |
| 6,579,231 B1 | 6/2003 | Phipps |
| 6,604,115 B1 | 8/2003 | Gary et al. |
| 6,633,772 B2 | 10/2003 | Ford |
| 6,638,073 B1 | 10/2003 | Kazimirov et al. |

| | | |
|---|---|---|
| 6,647,252 B2 | 11/2003 | Smith et al. |
| 6,656,127 B1 | 12/2003 | Ben-Oren et al. |
| 6,687,523 B1 | 2/2004 | Jayaramen et al. |
| 6,699,194 B1 | 3/2004 | Diab et al. |
| 6,702,752 B2 | 3/2004 | Dekker |
| 6,709,402 B2 | 3/2004 | Dekker |
| 6,721,594 B2 | 4/2004 | Conley et al. |
| 6,723,055 B2 | 4/2004 | Hoffman et al. |
| 6,726,636 B2 | 4/2004 | Der Ghazarian et al. |
| 6,727,197 B1 | 4/2004 | Wilson et al. |
| 6,736,759 B1 * | 5/2004 | Stubbs et al. ............ 482/8 |
| 6,747,561 B1 | 6/2004 | Reeves |
| 6,775,389 B2 | 8/2004 | Harrison et al. |
| 6,783,498 B2 | 8/2004 | Sackner et al. |
| 6,801,916 B2 | 10/2004 | Roberge et al. |
| 6,807,869 B2 * | 10/2004 | Farringdon et al. ...... 73/862.046 |
| 6,817,979 B2 | 11/2004 | Nihtila |
| 6,858,006 B2 | 2/2005 | MacCarter et al. |
| 6,881,192 B1 | 4/2005 | Park |
| 6,941,775 B2 | 9/2005 | Sharma |
| 6,961,448 B2 | 11/2005 | Nichols et al. |
| 6,970,731 B1 | 11/2005 | Jayaraman et al. |
| 6,993,378 B2 | 1/2006 | Wiederhold et al. |
| 7,001,337 B2 | 2/2006 | Dekker |
| 7,073,129 B1 | 7/2006 | Robarts et al. |
| 7,077,810 B2 | 7/2006 | Lange et al. |
| 7,081,095 B2 | 7/2006 | Lynn et al. |
| 7,082,327 B2 | 7/2006 | Houben |
| 7,099,714 B2 | 8/2006 | Houben |
| 7,104,962 B2 | 9/2006 | Lomask et al. |
| 7,154,398 B2 | 12/2006 | Chen et al. |
| 7,207,948 B2 | 4/2007 | Coyle |
| 7,254,516 B2 | 8/2007 | Case, Jr. et al. |
| 7,267,652 B2 | 9/2007 | Coyle et al. |
| 7,319,385 B2 | 1/2008 | Ruha |
| 7,413,546 B2 * | 8/2008 | Agutter et al. ............ 600/485 |
| 7,559,902 B2 | 7/2009 | Ting et al. |
| 7,604,603 B2 | 10/2009 | Sackner et al. |
| 7,670,295 B2 | 3/2010 | Sackner et al. |
| 7,727,161 B2 | 6/2010 | Coyle et al. |
| 7,762,953 B2 | 7/2010 | Derchak et al. |
| 7,809,433 B2 | 10/2010 | Keenan |
| 7,878,979 B2 | 2/2011 | Derchak |
| 7,920,144 B2 * | 4/2011 | Vogt et al. ............ 345/475 |
| 2002/0032386 A1 * | 3/2002 | Sackner et al. ............ 600/536 |
| 2002/0084130 A1 | 7/2002 | Der Ghazarian et al. |
| 2002/0090667 A1 | 7/2002 | Ratcliffe et al. |
| 2002/0123701 A1 | 9/2002 | Eriksen et al. |
| 2003/0100843 A1 | 5/2003 | Hoffman |
| 2003/0135097 A1 | 7/2003 | Wiederhold et al. |
| 2003/0135127 A1 | 7/2003 | Sackner et al. |
| 2003/0185408 A1 | 10/2003 | Causevic et al. |
| 2003/0187341 A1 | 10/2003 | Sackner et al. |
| 2004/0002634 A1 | 1/2004 | Nihtila |
| 2004/0010420 A1 | 1/2004 | Rooks |
| 2004/0019289 A1 | 1/2004 | Ross |
| 2004/0030224 A1 | 2/2004 | Sotos et al. |
| 2004/0111040 A1 | 6/2004 | Ni et al. |
| 2004/0117204 A1 | 6/2004 | Mazar et al. |
| 2004/0122334 A1 | 6/2004 | Yamashiro |
| 2004/0143194 A1 | 7/2004 | Kihara et al. |
| 2004/0167420 A1 | 8/2004 | Song et al. |
| 2004/0204636 A1 | 10/2004 | Diab et al. |
| 2004/0210147 A1 | 10/2004 | Houben |
| 2004/0225227 A1 | 11/2004 | Newman |
| 2004/0249299 A1 | 12/2004 | Cobb |
| 2005/0010117 A1 * | 1/2005 | Agutter et al. ............ 600/484 |
| 2005/0027207 A1 | 2/2005 | Westbrook et al. |
| 2005/0054941 A1 | 3/2005 | Ting et al. |
| 2005/0076908 A1 | 4/2005 | Lee et al. |
| 2005/0119586 A1 | 6/2005 | Coyle et al. |
| 2005/0125970 A1 | 6/2005 | Nolan |
| 2005/0139213 A1 * | 6/2005 | Blike ............ 128/205.23 |
| 2005/0211247 A1 | 9/2005 | Noda et al. |
| 2005/0228234 A1 | 10/2005 | Yang |
| 2005/0240087 A1 | 10/2005 | Keenan et al. |
| 2005/0256385 A1 | 11/2005 | Diab et al. |
| 2006/0000420 A1 | 1/2006 | Martin Davies |
| 2006/0036183 A1 | 2/2006 | Sackner et al. |
| 2006/0074334 A1 | 4/2006 | Coyle |
| 2006/0122528 A1 | 6/2006 | Gal |
| 2006/0178591 A1 | 8/2006 | Hempfling |
| 2006/0229917 A1 * | 10/2006 | Simske et al. ............ 705/3 |
| 2006/0258914 A1 | 11/2006 | Derchak |
| 2006/0293609 A1 | 12/2006 | Stahmann et al. |
| 2007/0027368 A1 | 2/2007 | Collins et al. |
| 2007/0100622 A1 | 5/2007 | Tavares |
| 2007/0150006 A1 | 6/2007 | Libbus et al. |
| 2007/0177770 A1 | 8/2007 | Derchak et al. |
| 2007/0208262 A1 | 9/2007 | Kovacs |
| 2007/0209669 A1 | 9/2007 | Derchak |
| 2007/0270671 A1 | 11/2007 | Gal |
| 2008/0015454 A1 | 1/2008 | Gal |
| 2008/0027341 A1 | 1/2008 | Sackner et al. |
| 2008/0045815 A1 | 2/2008 | Derchak et al. |
| 2008/0051839 A1 | 2/2008 | Libbus et al. |
| 2008/0082018 A1 | 4/2008 | Sackner et al. |
| 2008/0221401 A1 | 9/2008 | Derchak et al. |
| 2008/0269644 A1 | 10/2008 | Ray |
| 2009/0131759 A1 | 5/2009 | Sims et al. |
| 2010/0274100 A1 | 10/2010 | Behar et al. |
| 2011/0009766 A1 | 1/2011 | McCool |

FOREIGN PATENT DOCUMENTS

| | | |
|---|---|---|
| GB | 2116725 | 9/1983 |
| JP | 1091834 | 4/1989 |
| JP | 5168602 | 7/1993 |
| JP | 5298589 | 11/1993 |
| WO | WO 01/28420 | 4/2001 |
| WO | WO 01/29799 A2 | 4/2001 |
| WO | WO 01/76467 A2 | 10/2001 |
| WO | WO 02/37827 A2 | 5/2002 |
| WO | WO 02/060370 | 8/2002 |
| WO | WO 2004/019503 | 3/2004 |
| WO | WO 2005/016137 A1 | 2/2005 |
| WO | WO 2005/115242 | 12/2005 |
| WO | WO 2006/002338 | 1/2006 |
| WO | WO 2006/009830 A2 | 1/2006 |
| WO | 1 656 880 A1 | 5/2006 |
| WO | WO 2007/021645 | 2/2007 |
| WO | WO 2007/069111 A2 | 6/2007 |
| WO | WO 2007089751 | 8/2007 |
| WO | WO 2009/074973 | 6/2009 |
| WO | WO 2010027515 | 3/2010 |

OTHER PUBLICATIONS

Aliverti, A. et al., "Chronic Obstructive Pulmonary Disease: Regional Chest Wall Volumes During Exercise in Chronic Obstructive Pulmonary Disease." *Thorax*, 59:210-216, 7 pages, 2004.

Almeida et al., "Wavelet Transform Based Matlab System for the Detection and Delineation of QRS Complexes in Ambulatory ECG Recordingd", *6th Portuguese Conference on Biomedical Engineering* (Jun. 2001), 2 pages.

Anderer et al., "Artifact Processing in Computerized Analysis of Sleep EEG—A Review" *Neuropsychobiology*, 40:150-157 (1999), 8 pages.

Bianchi et al., "Extraction of the Respiration Influence From the Heart Rate Variability Signal by Means of Lattice Adaptive Filter", *IEEE Transactions on Biomedical Engineering*, pp. 121-122 (1994), 2 pages.

National Biometric Test Center, "The Functions of Biometric Identification Devices", *San Jose State University Biometrics Publications*, www.engr.sjsu.edu/biometrics/publications_tech.html (printed Jul. 28, 2005), 25 pages.

National Biometric Test Center, "Biometric Technology—Testing, Evaluation, Results", *San Jose State University Biometrics Publications*, www.engr.sjsu.edu/biometrics/publications_tech.html (printed Jul. 28, , 2005), 13 pages.

Blechert et al., "Identifying Anxiety States Using Broad Sampling and Advance Processing of Peripheral Physiological Information," *Phychosom Med* Dec. 2007;69(9):935-43 Epub Nov. 8, 2007, 6 pages.

(56) References Cited

OTHER PUBLICATIONS

Bloch et al., "Specific respiratory patterns distinguish among human basic emotions," *International Journal of Psychophysiology*, 11:141-154 (1991), 14 pages.
Bonnet et al., "EEG Arousals: Scoring Rules and Examples, A Preliminary Report from the Sleep Disorders Atlas Task Force of the American Sleep Discorders Association," *Sleep*, 152(2): 173-184 (1992), 12 pages.
Brack, "Cheyne-Stokes respiration in patients with congestive heart failure," Swiss Med Weekly 133:605-610 (2003), 7 pages.
Costa et al., "Multiscale Entropy Analysis of Complex Physiologic Time Series," Physical Review Letters 89(6):068102-1-4 Aug. 5, 2002, 4 pages.
Coyle et al., "Home Measurement of Cough Indicates Circadian Frequency Pattern and Abnormal Distribution During Sleep," LifeShirt, study sponsored by Pfizer, Inc., Jun. 2004, 1 page.
Gore Electronic Products, "Expanded PTFE Insulation Material", www.goreelectronics.com (visited Aug. 2005), 4 pages.
Grossman et al., "Reliability of Respiratory Tidal Volume Estimation by Means of Ambulatory inductive Plethysmography," Biomed Sci Instrum 42:193-8 (2006), 6 pages.
Grossman et al., "A Comparison of Three Quantification Methods for Estimation of Respiratory Sinus Arrhythmia", Psychophycology, 27(6):702-714 (1990), 17 pages.
Istepanian et al., "Microcontroller-Based Underwater Acoustic ECG Telemetry System", IEEE Transactions on Information Technology in Biomedicine, 1(2):150-154 (Jun. 1997), 5 pages.
Keenan et al., "Adaptive Filtering of Heart Rate Signals for an Improved Measure of Sympathovagal Balance," Jan. 1, 2005, 8 pages.
Klabunde, "Electrocardiogram (EKG, ECG)", Cardiovascular Physiology Concepts, www.cvphysiology.com (visited Mar. 2005), 3 pages.
Lake et al., "Sample entropy analysis of neonatal heart rate variability," Am J Physiol Regul Integr Comp 283:R789-97 (2002), 10 pages.
Marin et al., "Inspiratory Capacity, Dynamic Hyperinflation, Breathlessness, and Exercise Performance During the 6-Minute-Walk Test in Chronic Obstructive Pulmonary Disease", Am. J. Respir. Crit. Care Med., vol. 163., pp. 1395-1399, (2001), 5 pages.
McCool et al., "Estimates of ventilation from body surface measurements in unstricted subjects," J. Appl. Physiol. 61(3):1114-9 (1986), 6 pages.
McCool et al., "Tidal Volume and Respiratory Timing Derived From a Portable Ventilation Monitor," Chest 122:684-91 (2002), 10 pages.
McNaughton et al., "Metallized Polymer Fibers as Leadwires and Intrafascicular Microelectrodes", J. Neurosci. Methods, 70(1):103-10 (1996). 2 pages.
Micro-Coax, "About Micro-Coax", www.micro-coax.com (visited Aug. 2004), 9 pages.
Niskanen et al., "Software for Advanced HRV Analysis", University of Kuopio Department of Applied Physics Report Series, pp. 1-11 (Feb. 2002), 12 pages.
O'Donnell, "Ventilatory Limitations in Chronic Obstructive Pulmonary Disease", Medicine & Science in Sports & Exercise, pp. S647-S655, (2001), 9 pages.
O'Donnell et al., "Dynamic Hyperinflation and Exercise Intolerance in Chronic Obstructive Pulmonary Disease", Am. J. Respir. Crit. Care Med., 164:770-777 (2001), 8 pages.
Park et al., "Automated Detection and Elimination of Periodic ECG Artifacts in EEG Using the Energy Interval Histogram Method", IEEE Transactions on Biomedical Engineering 49(12):1526-1533 (2002), 8 pages.
Pietraszek et al., "Simple Telemetry System for ECG Recording", Polish J. Med. Phys. & Eng. 2002; 8(3): 193-198, 4 pages.
Rampil, "A Primer for EEG Signal Processing in Anesthesia," Anesthesiology 89(4):980-1002 Oct. 1998, 15 pages.
Richman et al., "Physiological time-series analysis using approximate entropy and sample entropy," Am J. Physiol Circ Physiol 278:H2039-49 (2000), 11 pages.
Signal Consulting Inc., "Inductance of Circular Loop", www.sigcon.com (visited Aug. 2005), 2 pages.
Sijbers et al., "Reduction of ECG and gradient related arifacts in simultaneously recorded human ERH/MRI data," Magnetic Resonance Imaging 18:881-6 (2000), 6 pages.
Snyder et al., "Ventilatory Responses to Hypoxia and High Altitude During Sleep in Aconcagua Climbers," Wilderness and Environmental Medicine 18:138-145 (2007), 8 pages.
Szabo et al., "Prognostic Value of Heart Rate Variability in Chronic Congestive Heart Failure Secondary to Idiopathic or Ischemic Dilated Cardiomyopathy," Am J Cardiol. 79:978-980 (1997), 3 pages.
van Dijk et al., "Determinants of Brachial Artery mean 24 h PulsePressure in Individuals with Type II diabetes mellitus and untreated mild hypertension", Clinical Science (2002), 102, pp. 177-186, 10 pages.
Vogiatzis, et al., "Respiratory Kinematics by Optoelectronic Plethysmography During Exercise in Men and Women.", Eur J of App Physiol, 581-587, 7 pages, 2004, 7 pages.
Wilhelm et al., "Distinguishing Emotional From Physical Activation in Ambulatory Psychophysiological Monitoring," Biomed Sci Instrum 42:458-63 (2006), 6 pages.
Wilheim et al., "Taking the laboratory to the skies: Ambulatory assessment of self-report, autonomic, and respiratory responses in flying phobia," Psychophysiology 35:596-606 (1998), 11 pages.
International Search Report and the Written Opinion of the International Searching Authority, application No. PCT/US06/60264, dated Jan. 15, 2008, 8 pages.
International Search Report and the Written Opinion of the International Searching Authority, application No. PCT/US2007/82688, dated May 8, 2008, 7 pages.
International Search Report and the Written Opinion of the International Searching Authority, application No. PCT/US2008/072414, dated Nov. 12, 2008, 7 pages.
International Search Report and the Written Opinion of the International Searching Authority, application No. PCT/US2008/061171, dated Nov. 14, 2008, 10 pages
Supplementary Partial European Search Report of the European Patent Office Application No. EP 06784447.2, dated Jan. 20, 2010, 9 pages.
Extended European Search Report for Application No. EP 07798146.2, Applicant: adidas AG, mailed Oct. 19, 2010.
Extended European Search Report for Application No. EP 10174873.9, Applicant: adidas AG, mailed Dec. 8, 2010.
Extended European Search Report for Application No. EP 10174680.8, Applicant: adidas AG, mailed Dec. 9, 2010.
Extended European Search Report for Application No. EP 10174876.2, Applicant: adidas AG, mailed Dec. 9, 2010.
Extended European Search Report for Application No. EP 10174881.2, Applicant: adidas AG, mailed Dec. 9, 2010.
Extended European Search Report for Application No. EP 10174683.2, Applicant: adidas AG, mailed Dec. 27, 2010.
Partial European Search Report for Application No. EP 10174885.3, Applicant: adidas AG, mailed Jan. 4, 2011.
Office Action dated Aug. 2, 2010 from U.S. Appl. No. 11/373,822, Sackner, System and Methods for Ambulatory Monitoring of Physiological Signs, filed Mar. 9, 2006.
Office Action dated Sep. 28, 2010 from U.S. Appl. No. 11/503,350, Behar, Systems and Methods for Monitoring Subjects in Potential Physiological Distress, filed Aug. 10, 2006.
Office Action dated Oct. 15, 2010 from U.S. Appl. No. 11/627,198, Derchak, System and Method for Identity Confirmation Using Physiologic Biometrics to Determine a Physiologic Fingerprint, filed Jan. 25, 2007.
Office Action dated Jan. 4, 2011 from U.S. Appl. No. 11/233,317, Gal, Improved Sensors for Inductive Plethysmographic Monitoring Applications and Apparel Using Same, filed Sep. 21, 2005.
Office Action dated Jan. 27, 2011 from U.S. Appl. No. 10/991,877, Keenan, Method and system for processing data from ambulatory physiological monitoring, filed Nov. 18, 2004.
Office Action dated Feb. 2, 2011 from U.S. Appl. No. 11/373,822, Sackner, System and Methods for Ambulatory Monitoring of Physiologial Signs, filed Mar. 9, 2006.

(56) References Cited

OTHER PUBLICATIONS

U.S. Appl. No. 11/357,772, Sackner, System and Methods for Ambulatory Monitoring of Physiological Signs, filed Feb. 17, 2006.
U.S. Appl. No. 11/373,822, Sackner, System and Methods for Ambulatory Monitoring of Physiological Signs, filed Mar. 9, 2006.
U.S. Appl. No. 12/869,576, Stone, Method and System for Limiting Interference in Magnetometer Fields, filed Aug. 26, 2010.
U.S. Appl. No. 12/869,578, Derchak, Noninvasive Method and System for Monitoring Physiological Characteristics, filed Aug. 26, 2010.
U.S. Appl. No. 12/869,582, Derchak, Noninvasive Method and System for Monitoring Physiological Characteristics and Athletic Performance, filed Aug. 26, 2010.
U.S. Appl. No. 12/869,585, Derchak, Noninvasive Method and System for Monitoring Physiological and Athletic Performance Characteristics of a Subject, filed Aug. 26, 2010.
U.S. Appl. No. 12/869,586, Derchak, Physiological Database and System for Population Modeling and Method of Population Modeling, filed Aug. 26, 2010.
U.S. Appl. No. 12/869,592, Derchak, Multimodal Method and System for Transmitting Information About a Subject, filed Aug. 26, 2010.
U.S. Appl. No. 12/869,625, Derchak, Method and System for Interpretation and Analysis of Physiological, Performance, and Contextual Informaton, filed Aug. 26, 2010.
U.S. Appl. No. 12/869,627, Derchak, Physiological Monitoring Garment, filed Aug. 26, 2010.
U.S. Appl. No. 12/872,174, Derchak, Physiological Monitoring Garment, filed Aug. 31, 2010.
U.S. Appl. No. 12/971,193, Sackner, Systems and Methods for Ambulatory Monitoring of Physiological Signs, filed Dec. 17, 2010.
U.S. Appl. No. 12/976,080, Derchak, Methods and Systems for Monitoring Respiratory Data, filed Dec. 22, 2010.
Fahrenberg, "Origins and Developments of Ambulatory Monitoring and Assessment", in Fahrenberg et al., 2001, Progress in Ambulatory Assessment Seattle, WA: Hogrefe and Huber.
Wachowski, Andy and Larry. The Matrix, released Mar. 31, 1999 by Warner Bros. Pictures. See 1:26:29, 2:03:10, and 2:04:41.
European Search Report for EP Application No. EP 12 16 3159, Munich, Germany, mailed on Jul. 30, 2012, 7 pages.

\* cited by examiner

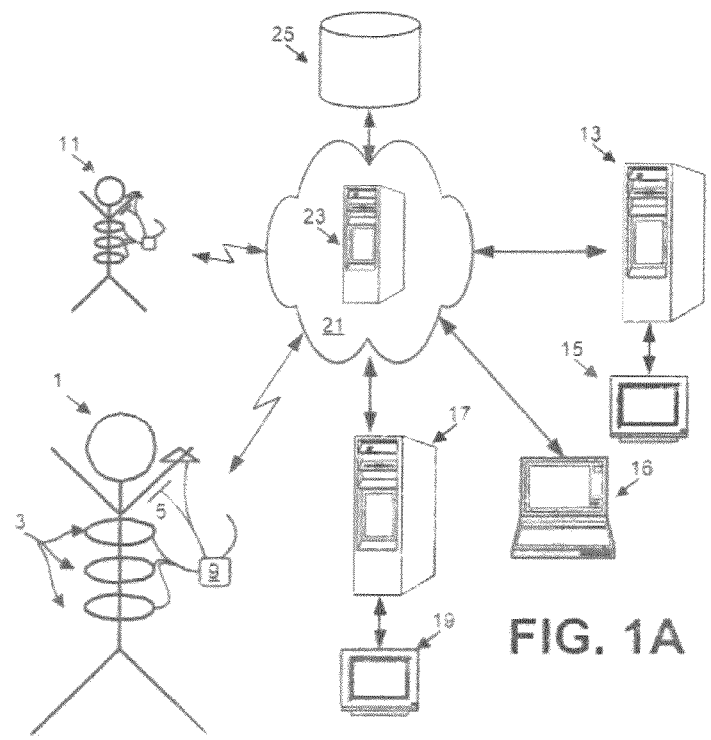
FIG. 1A
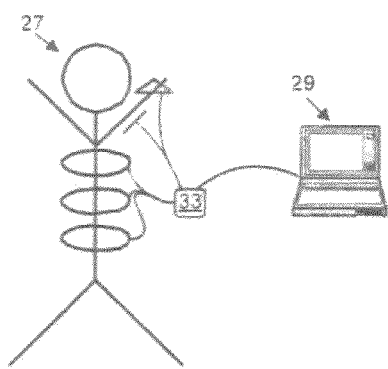
FIG. 1B1
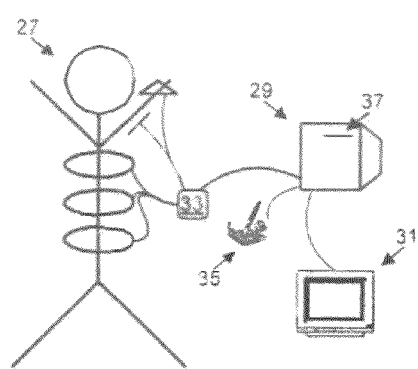
FIG. 1B2

COMPUTER INTERFACES INCLUDING PHYSIOLOGICALLY GUIDED AVATARS

CROSS REFERENCE TO RELATED APPLICATIONS

This application is a Continuation of U.S. application Ser. No. 11/492,484, filed 2006 Jul. 24, now pending; which claims the benefit of prior U.S. provisional application 60/702,779, filed Jul. 26, 2005.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to the field of graphical user interfaces for computer displays, and more particularly to graphical interfaces for visualizing physiological data by means of avatars.

BACKGROUND OF THE INVENTION

Traditionally, physiological monitoring could only be performed in the clinic, hospital, or laboratory using monitoring equipment that was often not portable and could even be invasive. As a consequence, physiological monitoring was limited and the resulting data generally available only to trained personnel. Consequently, physiological data displays were designed primarily for such personnel.

However, advances in physiological monitoring now permit the monitoring of persons in a wide range of environments. For example, it is now possible to obtain cardiopulmonary data in real time using non-invasive sensors and lightweight monitoring devices from unrestrained, ambulatory persons going about their normal activities. An example of an ambulatory monitoring system is described in U.S. Pat. No. 6,551,252 B1, issued Apr. 23, 2003. This patent describes systems and methods that use comfortable garments as platforms for sensors of multiple physiological parameters. Sensor data can be processed at the monitored person or transmitted or stored for remote processing.

Although physiological monitoring data is now more available, even to persons without training, physiological data displays are still often designed, as they were in the past, for trained personnel. Such displays, however, can be difficult for non-trained persons. Their access to physiological monitoring data is thereby limited and new applications for such data are hindered.

A number of references are cited herein, the entire disclosures of which are incorporated herein, in their entirety, by reference for all purposes. Further, none of these references, regardless of how characterized above, is admitted as prior to the invention of the subject matter claimed herein.

SUMMARY OF THE INVENTION

This invention provides user interfaces displaying physiological information that are designed for both skilled and less skilled users, including those without specialized physiological or medical training. Preferred display interfaces include graphical elements that promote intuitive understanding of physiological monitoring information, e.g., avatars guided by physiological monitoring data. The invention also provides novel applications of these user interfaces, e.g., computer games with input of moment-by-moment player physiology. The invention can also be implemented on a variety of user electronic devices having displays, including a training simulator, a personal digital assistant, a handheld PC, a cell phone, an IPod™, a digital camera, a Blackberry®, a wrist mounted display, and a digital wrist watch.

Specifically, the systems and methods of this invention obtain physiological monitoring data from a monitored subject and display the monitoring data by means of one or more avatars that represent or simulate or mimic the monitored physiological functions. In preferred embodiments, the monitoring and displaying are real time, so that, for example, monitored subjects can view and interface with the avatars representing their current physiological functions. Alternatively, stored monitoring data is displayed. Such an embodiment is useful for those needing to review and/or monitor subjects' physiological status. The invention is useful for monitoring humans, horses, dogs, monkeys, other mammals, and other compatible vertebrate animals.

Thus the user interfaces of this invention have at least one avatar guided by physiological data from a monitored subject (human or animal) that represents and/or simulates and/or mimics physiological systems according to and in dependence on the physiological monitoring data measured in real-time or retrieved from a data store. The physiologically-guided avatars can represent a wide range of physiological systems including for example: cardiac rate, and/or cardiac stroke volume, and/or respiratory rate, and/or respiratory volumes, and/or posture, and/or activity level, and/or skin conductance, and/or skin temperature, and/or levels of stress or anxiety, emotional states, and the like.

Specific examples of avatars include the following. Cardiac physiology systems can be represented or simulated or mimicked by cardiac avatars appearing as a more or less realistic heart images that expand and contract as would a real actual heart along with (or proportional to) the monitored heart data. Cardiac avatars can also represent stroke volume by expanding and contracting with varying amplitudes. A cardiac avatar can provide cardiac sounds simulating (or derived from) actual heart sounds. Cardiac dysfunction can also be simulated or mimicked. For example, arrhythmias can be represented as a cardiac avatar pulsing in a manner corresponding to the arrhythmia; dysfunctional contraction that occurs in, for example, heart failure or myocardial infarction, can be represented by a heart avatar expanding and contracting in a manner simulating the dysfunction. Cardiac electrical activities in or deduced from a concurrent ECG (electrocardiogram) signal can be represented by, e.g., avatar colors varying with potential. ECG waveforms can also be displayed side by side with the avatar. Measures of cardiac stroke volume measures are preferably determined by thoracocardiography ("TCG") and can also be represented with avatar colors varying with stroke volume.

Respiratory systems can be represented by one or more avatars appearing as one or both lungs and/or the respiratory tract and/or the chest. These images can expand and contract in along with (or proportional to) a concurrently measured respiratory rate and/or with an amplitude proportional to concurrently measured respiratory volumes. When such monitoring data is available, differential activity of the right and left lungs can be represented by differential expansion and contraction amplitudes of the right and left lung avatars. A chest avatar can also expand and contract with the underlying respiratory system. For example, certain respiratory sensors, for example, with respiratory based on inductive plethysmography (respiratory IP) technologies, return measurements of rib cage and/or abdominal sizes that can be used to guide an avatar representing the chest and adjacent abdomen as well as the underlying subject respiration. A respiratory avatar can also provide respiratory sounds representing air flow, and also sounds representing coughs, sighs, and the like, when these events are observed.

Furthermore, respiratory and/or cardiac avatars can represent blood oxygenation data, such as can be measured by pulse oximeters and the like, by changing blood and/or vascular colors, for example, varying between red and blue. Vascular avatars, if present, can represent the oxygenation state in the pulmonary and/or central and/or peripheral vasculature.

A subject's posture and activity can also be represented by an avatar. Posture and activity information can be derived from accelerometer data and similar data. For example, highpass filtered accelerometer data primarily reflects activity level, while low-pass filtered data primarily reflects posture. Then, posture can be represented by an avatar comprising images of a person, perhaps more or less stylized, that is, for example, recumbent and/or sitting and/or standing. Activity level can be represented by a person avatar engaged in selected activity with corresponding intensities. For example, images of a person avatar walking and/or walking rapidly and/or running and/or climbing can represent the corresponding subject activity levels. Appropriate sounds can accompany postures and activities.

Avatars can also represent, simulate, or mimic less direct physiological information, For example, an avatar can represent subject stress, or subject anxiety levels, or subject emotional state by displaying stylized faces having facial expression intuitively and generally associated with levels states of emotion and/or stress and/or anxiety. Such an avatar can also use symbolic representations, for example, graphics of more or less elevated physical pressure and/or physical temperature, or even simply by colors, e.g., progressing from "cooler" greens to "hotter" reds. A further such avatar can represent indicia of energy expenditure and the like by images of fuel gauges, fires and the like. Such less direct physiological information is often derived from directly measured monitoring data by linear models, neural networks, expert systems, and the like. For example, indicia of stress and/or anxiety can be derived from characteristically elevated or changed respiratory activity, cardiac activity, skin conductance and/or temperature, EEG data, and so forth. Indicia of energy expenditure can be derived by combining cardiac, respiratory, and accelerometer data.

Although the user interfaces of this invention include at least one physiologically guided avatar, avatars not directly guided by physiological monitoring data can also be presented. One such embodiment is directed to personal training, such as medical rehabilitation, athletic training, endurance training, and the like. Such an embodiment can present directly to the subject and in real time avatars that are physiologically-guided by a monitored subject during their training. The subject thereby receives a form of training or athletic biofeedback. A system for practicing this embodiment preferably includes wireless transmission of monitoring data from the subject and a training device, e.g., a stationary bicycle, or a treadmill, or the like, having a display for presenting such avatars.

Further, information regarding training progress and goals can be similarly presented to the subject. Progress and goal information can optionally be presented also as one or more avatars, e.g., a person avatar can act as a "virtual trainer" or a "virtual doctor". In the context of athletic training, a "virtual trainer" avatar can present a subject's training program and/or a subject's training accomplishments and/or a subject's current training goals. A "virtual trainer" avatar may also exhort the subject to further training achievements. In the context of rehabilitation, a "virtual doctor" avatar can be present similar information regarding a rehabilitation program, e.g., for myocardial infarction victims. Such an avatar can also be guided, e.g., by simple thresholds, by an expert system, or the like, to monitor for excessive physiological performance that may be risky. interpretations of monitoring data in order to suggest relevant medical issues and resolutions using text or text-to-speech outputs.

Other avatars can also be directly controlled by input from a user and/or a subject entered using mice, joysticks, game consoles, spoken input, and so forth. Directly controlled avatars can move and act in the user interface and can be particularly useful for, e.g., computer games that include player physiological information, Furthermore, the user interfaces of this invention can have the following additional features. An avatar can have alternate visual realizations, for example, changing colors or sizes in response to status of a represented physiological system. An avatar can include multimedia elements, e.g., sound presentations as well as visual presentations. Sounds can simulate or mimic sounds normally generated by a monitored physiological system, or can include spoken text summarizing monitoring data, or can draw attention to important situations, and the like. An avatar can from time-to-time have only a sound presentation, or only a visual presentation, or a combined sound and visual presentation., which can be presented to a user in selectable combinations.

User interfaces of this invention can also present two or more avatars. Different avatars can be guided different physiological functions monitored from a single subject, or by physiological monitoring data from two or more different subjects, and the like. Different avatars can be combined as well as individually displayed. For example, a heart avatar guided cardiac monitoring data can be combined with a respiratory avatar guided by respiratory monitoring data to present a cardio-respiratory avatar guided by both cardiac and respiratory data. A cardio-respiratory avatar can be visually combined with a breathing chest, and all can be further combined with a person avatar representing subject posture and/or activity.

User interfaces of this invention can also include other visual elements. Avatars can be displayed against a background such as simple colors and/or textures, or stylized common environments such as a medical environment, or residential environment, or gym environment, or an athletic environment, GPS information from the monitored wearer information, geographical images (e.g., a satellite image based on GPS information), or the like. User interfaces can also include textural and/or numeric elements. For example, numeric values of monitored physiological data can be displayed as, e.g., thermometers, dials, sliders, and so forth. Quantitative data can be converted into text phrases or sentences which can be displayed or spoken. Further, multiple monitored subject can be presented as multiple avatars. For example, a team of first responders, e.g., a hazardous material clean up team of 25 or 50 people, can each be represented by a unique avatar displayed on a screen and representing the deployment of the team is deployed and the health status of each person.

This invention also includes virtual reality ("VR") type user interfaces in which avatars can act and/or move in a simulated 3D manner. A user or subject can then feel actively immersed in the physiology being represented. User interface displays can also be arranged so that the monitored subjects can view their own physiologically-guided avatars, preferably in real time. Immediate feedback can be used for physical training, or athletic training, or biofeedback, or the like.

Preferably, this invention's user interfaces and methods are made available on the widest possible range of computer systems, from low-end business and home PC-type computers to systems with advanced graphics capabilities. This invention can also be implemented on gaming systems such as a Playstation®, an X Box®, a wrist mounted low resolution display, a helmet mounted head's up displays with monocles and displays. These interfaces can also be used on handheld devices, e.g., handheld game machines, cell phones, PDAs, and the like. Examples of implementation systems include PC-type computers configured for home or business use can have processors with speeds of 1 GHz or lower and memories of 128 MB or lower. Implementation systems also include more capable PC-type computer systems can have processors with speeds of 2 GHz or greater and memories of 256 MB or more and be configured with add-in graphics boards enhanced processing and graphics capabilities. Implementation systems also include game processors or game machines, which now have highly capable graphics systems, using a TV set as a display. It is also preferred that this invention be implemented on high-performance work-station type computer systems with attached graphics subsystems perhaps, e.g., VR-type interfaces.

To provide for a range of implementation platforms it is preferred that this invention include a range of method implementations. These implementation are preferably structured in a client server fashion where in general the client displays the user interface including physiologically-guided avatars while the server generates and transmits the graphics to the client. The distribution of processing between client and server depends on client capabilities. For clients of limited capability, the server generates most graphics and transmits them to the client either in advance of user interface display (e.g., as a program product on removable computer readable media) or concurrently with user interface display. More capable client systems can also generate some displayed graphics in addition to interface display and require less server support. Finally, the most capable clients can generate substantially all displayed graphics and therefore can dispense with a server.

Accordingly, embodiments of this invention directed to low-end gaming and PC-type systems preferably perform little if any graphics generation, and instead retrieve and display already most avatar images already generated on a server, which for example, can be stored as animation sequences, such as an animation of a heart through one cycle from systole to diastole and back to systole. Preferably, even these clients have capabilities sufficient to modify graphics to some degree. For example, the client preferably is able to compose screen displays from already-created graphics objects, and/or display avatar animations at a rate guided by physiologically monitoring data and/or combine avatars with a selected background and other data, and so forth.

Embodiments directed to client systems of intermediate graphics capability can create or modify certain graphics but may still rely on a server for already-created graphics. For example, already-created images of a cardiac avatar can be morphed (i.e., smoothly changing an initial shape into a final shape) to represent, e.g., varying stroke volumes, or to simulate or mimic less predicable cardiac rhythms, such as ectopic ventricular beats, intermittent atrial tachycardia, and the like. Such clients can optionally generate user or subject controlled avatars, provide more backgrounds with size, view point, perspective, and the like.

Embodiments directed to high performance processing, graphics and display client systems can create all or nearly all graphics, in particular avatar images de novo, entirely from, e.g., object descriptions. Object descriptions can be parameterized so that avatars can be specifically generated to represent, simulate, or mimic current details of received physiological monitoring data. Also, aspects of the above range of embodiments can be combined.

The meanings and limitations of the terms "avatar" and "physiologically-guided avatar" as used herein are next described and illustrated with the assistance of non-limiting examples of cardiac avatars, which are displayed in some preferred embodiments to simulate, or mimic, or represent a subject's (human or animal) cardiac function and cardiac system. Cardiac avatars preferably comprise a sequence of heart images constructed and displayed in dependence on physiological monitoring data, which in the case of the cardiac system, is primarily cardiac rate and optionally also cardiac volume. Other avatars of this invention are similar.

In a simple cardiac avatar embodiment, a single cardiac avatar comprising a single sequence of cardiac images representing a pulsing heart is used to represent all monitored subjects. The image sequence can optionally be modified from, or derived from, a single original heart image. The avatar image sequence can then be displayed at a rate similar to a subject's concurrently monitored heart rate. Optionally, the image sequence can also be modified so that the displayed pulsation amplitude is similar to the subject's concurrently monitored cardiac stroke volumes (or indicia thereof).

A more complex cardiac avatar embodiment can use multiple differently-appearing cardiac avatars, the particular avatar used for a particular subject being chosen to best represent certain, selected characteristics of that subject's heart. For example, one embodiment can have four heart avatars: one heart avatar representing a young heart; another heart avatar representing an old heart; another heart avatar representing a healthy heart, and a further heart avatar representing a failing heart. Then, a young, old, healthy, or failing heart avatar is used to represent a young subject, an old subject, a healthy subject, or a subject suffering from heart failure, respectively. This embodiment represents more realistically than the previous embodiment selected cardiac characteristics.

An even more complex cardiac avatar embodiment can use a different avatar individualized for each monitored subject. For example, a medical image of a particular subject's (human or animal) heart, such as an MRI (magnetic resonance imaging) image or a CAT (computer assisted tomography) scan image, can be obtained. The cardiac avatar images for that subject can then comprise images, derived from, or modified from the medical image, each image perhaps being morphed by dilation and/or contraction of the original image in order to represent the subject's heart at one moment of a cardiac cycle having a particular stroke volume. This individualized avatar is then displayed at a rate determined by the subject's concurrently monitored heart rate and/or with an amplitude determined by the subject's concurrently monitored stroke volume. This embodiment is even more realistic.

It can now be appreciated that the avatars of this invention are neither medically-correct images nor mere cartoon-like animations. First, although avatar images in certain embodiments of this invention can be derived and modified from medically-correct images (e.g., MRI image, CAT images, medical photographs, and the like), the displayed avatar images do not provide images of a monitored subject that are medically-correct and useful. Medical images useful to a practitioner necessarily provide all image details in an entirely faithful manner. The avatars of this invention do not faithfully depict all medical details. Instead, they provide intuitively accessible, visual analogies for the physiology of a monitored subject as captured in physiological monitoring data. Second, although the avatars of this invention are visual analogues of a subject's monitored physiology, they are not entirely fanciful in the manner of cartoon-like animations and the like, even if certain cartoon-like animations provide similar visual analogies. Cartoon-like animations represent only the imagination of the creator. The avatars of this invention represent an actual monitored subject, and are guided the moment-by-moment actual by the subject's physiology.

A number of references are cited herein, the entire disclosures of which are incorporated herein, in their entirety, by reference for all purposes. Further, none of these references, regardless of how characterized above, is admitted as prior to the invention of the subject matter claimed herein.

BRIEF DESCRIPTION OF THE DRAWINGS

The present invention can be understood more fully by reference to the following detailed description of preferred embodiments of the present invention, illustrative examples of specific embodiments of the invention, and the appended figures in which:

FIGS. 1A, 1B1 and 1B2 illustrate exemplary systems for practicing this invention;

DETAILED DESCRIPTION OF THE PREFERRED EMBODIMENTS

Figure 2A:
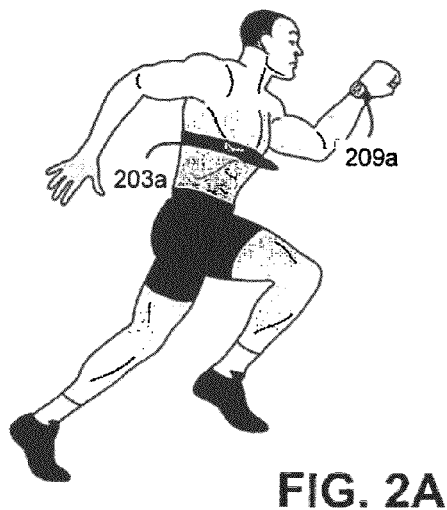
FIGS. 2A-C illustrate exemplary physiological monitoring sub-systems for practicing this invention.

This invention creates and displays user interfaces including avatars having actions guided by physiological data obtained by monitoring one or more subjects. Thus, such avatars are often referred to herein as "physiologically-guided avatars". In preferred embodiments, this invention can be practiced on PC-type computer systems. From the following description, it will be apparent to those of ordinary skill in the art how this invention can be implemented on other types of computer systems having other graphics capabilities. Headings are used hereon for clarity and convenience only and without any intended limitation.

Preferred Systems—Monitoring Subsystems

Preferred systems of this invention include sub-systems that collect physiological monitoring data from monitored subjects (monitoring sub-systems), and sub-systems that receive monitoring data and process it for display in the user interfaces of this invention (processing and/or display sub-systems). Generally, physiological monitoring sub-systems can be designed for in-hospital, in-clinic, and/or ambulatory use and can use either invasive and/or non-invasive sensors. Preferred monitoring subsystems are designed primarily for ambulatory use and have only non-invasive sensors.

FIGS. 1A, 1B1 and 1B2 schematically illustrate alternative system configurations. FIGS. 1B1 and 1B2 use the same reference numbers for the same structures, except for the replacement of computer 29 with device 30. These figures illustrate monitored subjects 1, 11, and 27 configured with exemplary, ambulatory and non-invasive physiological monitoring systems having exemplary physiological sensors 3 and 5. Sensors 3 are exemplary "size sensors". Such sensors are responsive to various indicators of body sizes, such as surface lengths, full or partial circumferences, diameters, and the like, and, when positioned on or about portions of a subject, can provide data responsive to the subject's physiological processes. For example, size sensors at one or more cross-sections of the torso, e.g., at an abdominal cross-section and at a rib cage cross section, provide data that can be accurately interpreted using a two-component breathing model to determine respiratory rates and volumes, e.g., tidal volumes. Size sensors at other torso cross sections provide data responsive to cardiac or aortic pulsations, and size sensors about one or more limbs can be responsive to venous or arterial pulsations.

Size sensors useful in the present invention can be based on diverse technologies, including magnetometers; strain gauges using magnetic, mechanical or optical means; optical techniques including interferometry; electrical impedance; surface electrical or magnetic activity; plethysmography, ultrasonic and Doppler measurements of body wall motions or body diameters; and so forth. Preferred size sensors are based on inductive plethysmographic (IP) technology. This technology uses sensors that have inductances that vary as the sizes of the sensors vary. Each IP sensor is coupled to an oscillator in a manner such that the oscillator frequency varies as sensor inductance varies. The output IP signal is a digitized representation of the varying oscillator frequency. Consequently, when an IP sensor is snugly fit to a body part, the resulting IP signal reflects the varying sizes of that body part.

IP technology has been described in U.S. patents assigned to the assignee of the present application, including U.S. Pat. Nos. 6,783,498; 6,551,252; 6,413,225; 6,341,504; 6,047,203; 5,331,968; 5,301,678; 5,178,151; 4,834,109; 4,807,640 issued Feb. 28, 1989. IP technology is also described in published U.S. Applications including application Ser. No. 10/822,260. Specialized IP technology known as thoracocardiography ("TCG") can also obtain measures of cardiac stroke volume, aortic pulses, and other central vascular pulsations. See specifically, e.g., U.S. Pat. Nos. 6,783,498 and 5,178,151. All U.S. patents and published U.S. applications referred to herein are incorporated herein by reference in their entireties for all purposes.

Sensor 5 represents other non-invasive physiological sensors that can be used in this invention. For example, accelerometers mechanically coupled to a monitored subject can register current activity level and posture of the individual's body or parts thereof. Electrodes electrically coupled to a monitored subject can register electrical activities including, e.g., electrocardiogram ("ECG") signals, electroencephalogram ("EEG") signals, electro-oculogram ("EOG") signals, electro-myogram ("EMG") signals, skin conductance or resistance, electrical impedances, and the like. Other sensors can register surface temperature, core temperature, blood oxygen saturation, generated sound, ultrasound signals and echoes, and the like.

The exemplary monitoring subsystems illustrated in FIG. 1A-B also includes portable data units (PDU), e.g., PDUs 9 and 33. PDUs contain electrical circuitry that operates sensors, retrieves sensor data, and processes retrieved data at least so that it can be digitally transmitted in real time. Preferred PDUs are sufficiently small and light so that they can be on or in the vicinity of the monitored subject. FIG. 1A illustrates wireless transmission, e.g., using Bluetooth, WiFi, or cell phone technologies. FIGS. 1B1 and 1B2 illustrates transmission via a wired link. Temporary storage if needed can use semiconductor or magnetic media.

Figure 2B:
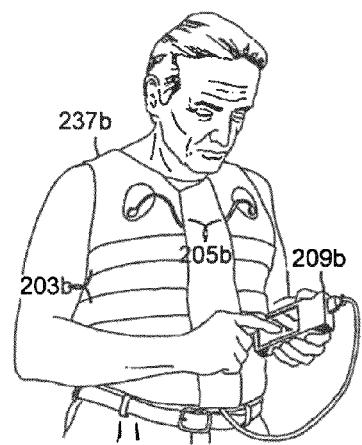
Figure 2C:
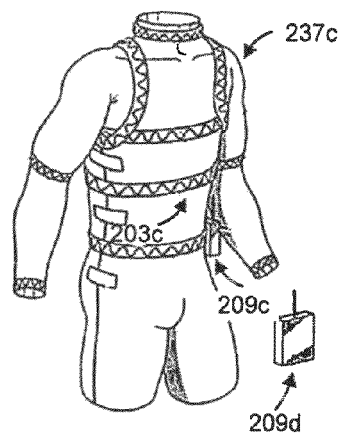

Preferred monitoring sub-systems configure sensors into one or more wearable items, for example, garments, jackets, bands, patches, and the like. The wearable items, e.g., garments, are preferably unobtrusive, comfortable, and useable without assistance. FIGS. 2A-C illustrate several monitoring garments. The subject of FIG. 2A is actively exercising unconstrained by a monitoring sub-system consisting of a single chest band 203a and local portable data 209a unit configured as a wrist watch. FIG. 2B illustrates a shirt 237b capable of incorporating more sensors but still suitable for most levels of activity. Illustrated are two size sensors 203b at the rib cage (RC) and the abdomen (AB) sizes that return signals from which tidal volume can be determined. The shirt also incorporates (a two lead) ECG 205b.

Finally, FIG. 2C illustrates garment 237c configured as a body suit and equipped with a more extensive array of size sensors 203c for measuring respiration rate and tidal volume, individual lung functioning, venous and arterial pulsations, cardiac volumes, individual lung function, and the like. This embodiment is provided with two portable data units, unit 209c attached to the garment for shorter range wireless transmission and limited signal storage and unit 209d in the vicinity of the garment for longer range wireless transmission and more extensive data storage.

In FIGS. 1A, 1B1, 1B2, and 2C, the upper and lower circles or bands about the thorax represent rib cage and abdominal IP sensors which provide signals from which respiratory rate, tidal volume, and other respiration-related parameters can be extracted. The central circle or band about the mid-thorax represents a further IP sensor which provides signals from which cardiac stroke volume and other cardiac-related measures can be extracted by means of TCG.

Suitable monitoring subsystems based on IP sensor technology are available from VivoMetrics, Inc., Ventura, Calif.

Preferred Systems—Processing and Display Subsystems

Methods of this invention can be implemented on a range of processing and display processing subsystems. Exemplary processing subsystems are illustrated in FIGS. 1A, 1B1 and 1B2.

FIG. 1A illustrates a processing and display subsystem accommodating a plurality of simultaneously-monitored subjects, subjects 1 and 11, a plurality of processing and display subsystems, subsystems 13, 15-17, 19, and 23, and a plurality of network links. Each subject 1 and 11 is fit with a wearable item configured with one or more physiological sensors operated by PDU 9. PDU 9 then wirelessly transmits monitoring data to network 21, and network 21 then transfers monitoring data to the processing and display systems. Monitoring data can be stored in database 25.

Here, processing subsystems 13 and 17 with display 15 and 19 can be, for example, PC-type computers. Processing subsystem 16 can be a laptop-type computer with a built-in LCD display. Processing system 23 can be a workstation-type or a server-type computer. In this embodiment, the processing and display subsystems can local to or remote from the monitored subjects. Subsystems 16, 17 and 19 can be located in the vicinity of subject 1 so that this subject can view avatars representing simultaneous physiological functions in real time. Subsystems 13 and 15 can be remote from monitored subjects 1 and 11 for use by, e.g., medical personnel, monitoring personnel, or the like. All these processing and display subsystems display avatars representing monitored subjects and guided by real time or by previously-recorded monitoring data.

FIG. 1B1 illustrates an exemplary system for single monitored subject 27 who is illustrated wearing a garment with a plurality of sensors. The processing and display subsystems, to which the subject is directly linked by a wired connection through PDU 33, are a routine PC-type computer 29 and a routine PC-type display. Computer 29, perhaps being of more limited capabilities, may display physiologically-guided avatars easily constructed from graphic templates previously downloaded from a more capable server-type computer. FIG. 1B2 illustrates an similar system but adapted for computer games employing avatars guided by the physiology of the one or more players. This gaming embodiment employs as a processing subsystem 30 one of the commercial gaming systems, e.g., XBox™, Microsoft Corporation (Redmond, Wash.), PlayStation™, Sony Corporation of America (New York, N.Y.), and GameCube™, Nintendo of America Inc. (Redmond, Wash.). Modern commercial gaming systems can include processing and graphics capabilities sufficient to display physiologically-guided avatars having realistic images and realistic behaviors. Optionally, a gaming embodiment (and other embodiments) can display avatars guided by explicit user control from, e.g., gaming input device 35. Also, the display subsystem for a gaming embodiment (and other embodiments) can be a standard television set, a hand held electronic device, a hand held gaming device, a cell phone, and other portable electronic devices.

It should be understood from the above that this invention can be implemented on processing and display subsystems with a range of capabilities, subsystems of greater capabilities operating standalone while subsystems of lesser capabilities requiring assistance of server systems. For example, some processing and display subsystems can have sufficient processing and graphics capabilities to be able to create and display all graphics representing the physiologically-guided avatars of this invention. Other subsystems can have lesser capabilities sufficient only to create and display some, perhaps simpler, graphics representing physiologically-guided avatars. More complex graphics beyond such subsystems capabilities can be downloaded offline or online from server systems where these graphics are created. Finally, this invention can be implemented on subsystems of modest capabilities that require most graphics to be downloaded or preloaded from a server. Such subsystems may be limited to no more than displaying already-created animations.

Methods of the Invention

Methods of this invention first receive physiological sensor data, then extract physiological information from the received data, next create and/or modify user interface graphics including at least one avatar guided by the extracted physiological information, and finally display the created user interface. It has already been described in detail how data is received from physiological monitoring subsystems; the further steps of the methods of this invention are described in detail in the following.

The sensor signal processing needed to extract physiological information is known for many of the important sensors of use in this invention is known. For example, the processing required to extract respiratory rate and respiratory volume information from respiratory IP sensor signals, e.g., signals from IP sensors at the level of the rib cage and/or the abdomen, is described in the previously cited U.S. patents and applications that describe IP technology and that are assigned to the assignee of this invention. See, in particular, U.S. Pat. Nos. 6,551,252 and 6,047,203 and U.S. application Ser. No. 10/822,260. Heart rate information can be extracted from ECG signals by known methods. An IP sensor at the mid-thorax provides signals from which cardiac stroke volumes and cardiac output can be extracted according to methods also described in the cited IP patents, in particular in U.S. Pat. No. 6,783,498. Further, accelerometer data can be processed to provide posture and activity data. Cerebral electrical activity signals can be processed to yield electroencephalographic frequency spectrum information, from which in turn can a degree of alertness or arousal can be inferred. See, e.g., U.S. patent application Ser. No. 10/991,877 (and incorporated herein by reference in its entirety for all purposes). Body temperature signals, skin conductance signals, and the like, can often be processed by little more than filtering and artifact removal.

The graphics creation and display methods are preferably structured so that this invention can be implemented on user systems having a wide range of processing capabilities. A preferred such structure that achieves this goal separates these methods into a number of processing units that operate in, at least, a conceptually sequential manner and perhaps also in a temporally sequential manner. Then a user system can process only those final units in the processing sequence that are within its capabilities, while relying on server systems for processing of the prior processing units. For example, a highly capable user system may process all processing units, while a minimally capable user system may process only the terminal processing unit receiving the results of processing the prior unit from a server system. For clarity and without limitation, the methods of this invention are now described in the following in an embodiment where there are two principal processing units: a first unit that creates and renders graphics objects, and a second unit that assembles and displays already-created graphic objects.

Figure 3:
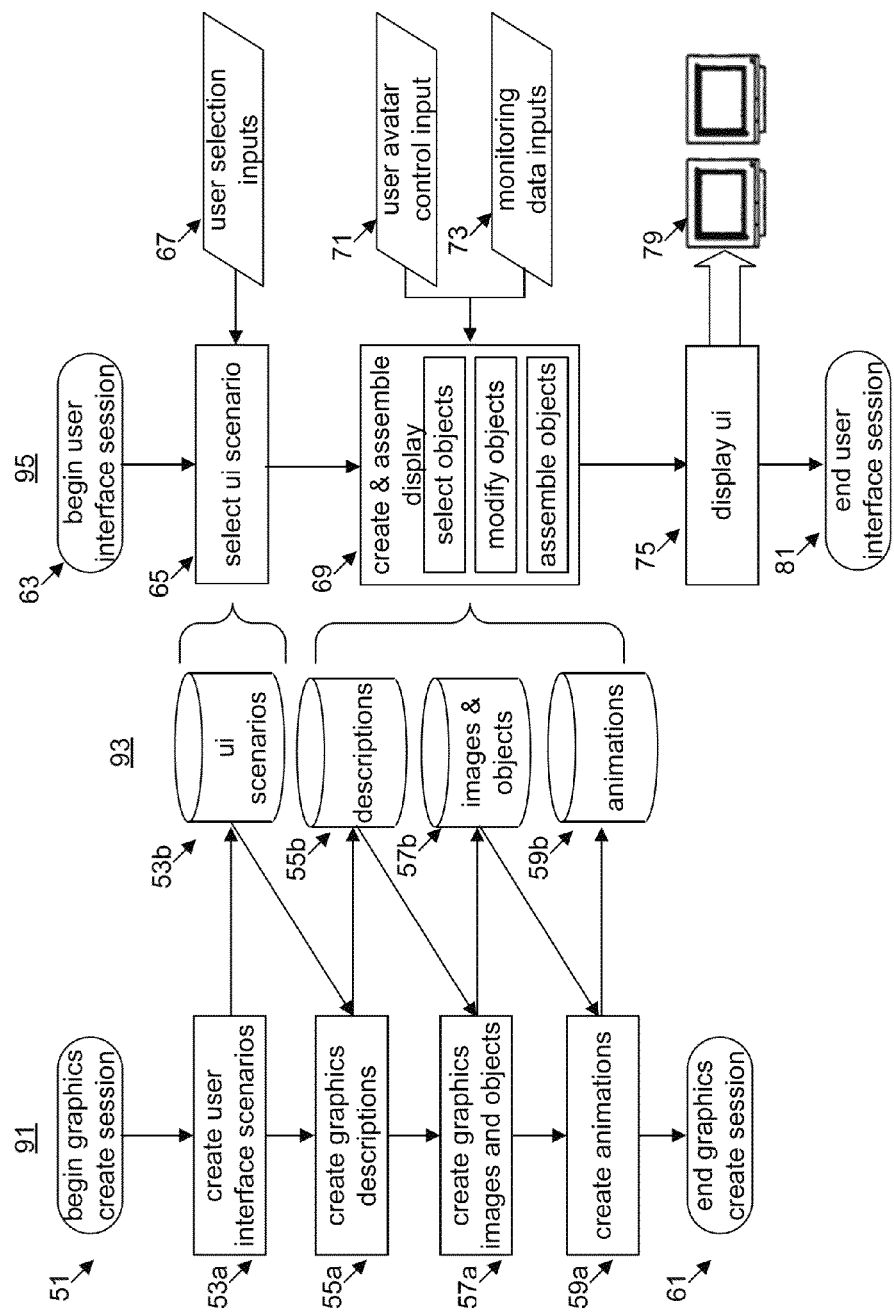
FIG. 3 illustrates schematically methods of this invention.

FIG. 3 illustrates such a preferred embodiment where the methods of this invention are structured into two units, create-graphics unit 91 and user-interface-session unit 95. The two processing units are linked by the exchange of graphics-related data represented as stores 93. Although stores 93 is illustrated as magnetic disk storage, this is exemplary and not limiting as graphics-related data can be exchanged also on optical media, by network link, in shared main memory (when a single system processes both units), or by other means known in the art. Generally, the create-graphics unit is performed first in order to create graphics data represented as in store 93. The user session unit is performed next (or overlaps or is pipelined with the create graphics unit). It retrieves the created graphics data, and uses it to assemble and display user interfaces with physiologically guided avatars. The term "user session" is used herein to conveniently refer to a group of sequential user steps.

Different embodiments can perform particular steps illustrated in FIG. 3 in different sequences. For example, a processor and display subsystem of greater capabilities can be able to perform step 59*a* and/or step 57*a* of the create-graphics sequence as part of the create-objects sub-step of create-and-assemble step 69. In this case, steps 59*a* and/or 57*a* need not be performed and stores 59*b* and/or 57*b* need not be created. However, a processor and display subsystem of lesser capabilities need only perform the create-and-assemble step to create displayable graphics data as illustrated, relying on already-created graphics data in store 93.

A create-graphics session proceeds step-by-step from begin 51 to end 61 to create and store increasingly detailed graphics descriptions and graphics objects. First, step 53*a* creates and stores 53*b* one or more user interface scenarios. User interface scenarios describe general user interface characteristics, e.g.: the types of avatars and by what physiological data they are guided, their visual representations, their behaviors, and the like. A scenario can include a series of scenes that also characterize display of textual, numeric, or symbolic information elements to be displayed in other than avatar formats, user interface background, the visual environment of avatar and non-avatar displays; and the like. User interface scenarios can be created de novo by, e.g., illustrators, animators, interface designers, and the like. Graphical representation can also be derived from graphics and image libraries, e.g., medical image libraries.

Next, in step 55*a*, graphics software creates and stores 55*b* graphic object descriptions from scenes and scenarios 53*a*. These descriptions are higher level (often non-displayable) instructions that rendering software can use to create displayable images. For example, one type of such description specifies a sequence of vectors that outline an image; another type can specify a plurality of triangles, surface colorings, and surface texturing that form a three-dimensional appearing image. These description can allow aspects of individual elements of these scenes, as well as the scene as a whole, are modifiable. For example, properties of individual elements such as scale, orientation, lighting, movement, and the like can be modified. Additionally, description of physiologically guided avatars or avatar elements must include information described how the individual display elements respond to physiological monitoring information. For example, in the case of a respiration-guided avatar image, the modifications of scene elements can be parameterized by, e.g., tidal volume. Such descriptions can be encoded as lists of, e.g., Open GL, parameterized commands.

Next, step 57*a* creates and stores 57*b* displayable graphic images and objects from graphic descriptions 55*b*. Displayable images can include bitmaps, bitmaps fragments, and the like that can be assembled into a complete image ready for presentation on a raster display device, These objects are generally built from the previous graphics descriptions, but can also include images retrieved from libraries of already-created objects and images. Displayable images such as bitmaps are generally less modifiable than graphic descriptions, For example, aspects of the scenes as a whole usually can be modified by, e.g., scaling, rotation, coloring, and the like, but aspect of individual scene elements cannot usually be individually modified. Accompanying these bitmaps and the like is information describing how they are controlled by physiological monitoring information. This information can control bitmap modification as such modification is possible. Alternatively, each bitmap can comprise a set of closely related bitmaps, and physiological monitoring information can select from this set Next, if called for by a particular scenario, step 59*a* creates and stores 59*b* animations for display in user interfaces. Animations are preferably constructed to be similar to movie clips comprising a sequence of images or frames that together represent avatar behaviors, or avatar behavior fragments. Modification of animations is generally limited to overall scaling, playback speed, modification of individual images, and the like. And animations include description of how these modifications (especially playback speed) are controlled by physiological monitoring information. Display of user interfaces constructed from avatar animations generally requires few client resources, limited to, e.g., assembly of one or more animations into a single interface and then playback of the assembled animations as guided by physiological monitoring data. For example, an animation can depict the right and left lungs as they proceed through an cycle of inhalation and exhalation cycle; this animation can be played back at the monitored rate of the subject's respiration.

User interfaces are assembled and displayed during a user-interface-session sequence which extends from begin 63 to end 81. First, a user initiates 67 a user interface (UI) session and selects 65 the desired user interface description from the already-created, libraries. Some embodiments can offer only one UI; in other embodiments can offer a plurality of UIs. The UI can be executed as a substantially independent program or be integrated into a parent application. In the case of a more capable user system, the user interface description can be a scenario selected from UI scenario store 53b, and the user system then entirely builds and modifies 69 all display images. In the case of a user system of limited capabilities, the user interface description can be an animation selected from store 59b, and the user system merely controls 69 its playback rate in response to physiological monitoring information.

Input necessary to control the physiologically-guided avatars and other controllable elements of the selected user interface is extracted from user monitoring data 73. Physiological monitoring data 73 can be received in real time from monitoring subsystems, or monitoring data can be stored and later retrieved. If one or more avatars or other UI components respond to user input 71, input from appropriate user interface devices is also necessary.

Next, the user interface is created and assembled 69 from the retrieved user interface description. As described, depending on the capabilities of the user system, the creation and assembly step can perform in essence one of more of steps 53a-59a. For example, a user system can perform all of 53a-59a, or only 55a-59a, or only 57a and 59a, or only 59a. In these case, stores 53a-59a can merely represent in-memory transfer of data between processes. Alternatively, a user system can merely retrieve already-created UI (perhaps from a removable storage device) and display them under the control of physiological monitoring data. As also described, graphic objects and data description include how they are parameterized and controlled by physiological monitoring data.

More concrete UI descriptions are generally less modifiable and controllable than more general UI descriptions. Thus, UIs created and assembled from stores 53b or 55b are capable or fuller, perhaps more realistic, depiction of a subject's physiological processes. And, for UIs selected and displayed from store 59a, only playback speed, overall shading, and the like can be controlled by monitoring data.

Finally, the created and assembled UI scenes are displayed 75. Steps 69 and 75 may be separate as illustrated, or alternatively, can be closely coupled into what is essentially a single step. The above description is one preferred embodiment of the methods of this invention that has been chosen and presented for compactness and clarity of description. It will be understood by one of ordinary skill in the art, that the invention includes alternative embodiments having methods with different structures and arrangements but that are capable of implementing the physiologically-guided avatars of this invention.

Software modules and accompanying graphics data objects are selected, packaged and provided to client and server systems according to their capabilities and/or available resources. Software methods can be written in appropriate computer languages, preferably C or C++, with graphics facilities provided by interlace libraries, e.g., OpenGL (OpenGL Foundation, www.opengl.org), DirectX (Microsoft, Inc.), and the like. Alternatively, software can be written in high level graphics-oriented languages, such as are provided by Macromedia, Inc. (San Francisco, Calif.). Executable software and graphics data can be provided to client and server systems on optical and magnetic storage media, or by network link, or by other known distribution means.

EXAMPLES OF THE INVENTION

Figure 4A:
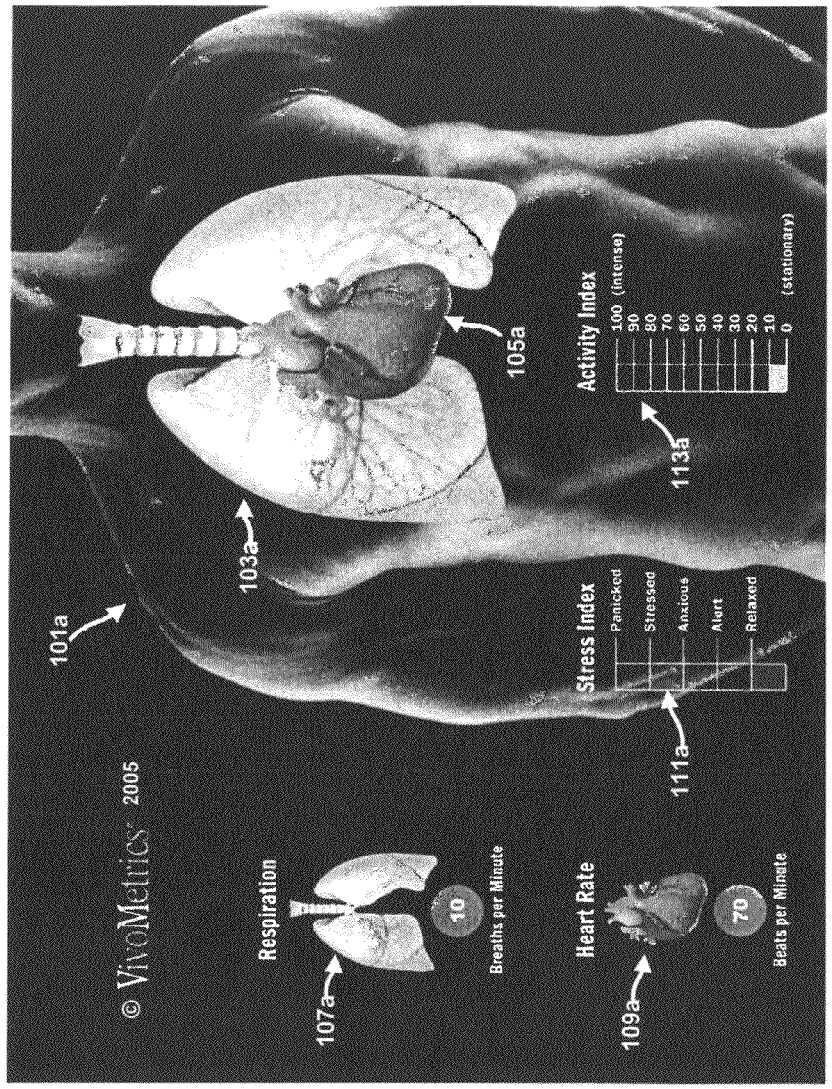
FIGS. 4A-B illustrate behaviors of an exemplary avatar.
Figure 4B:
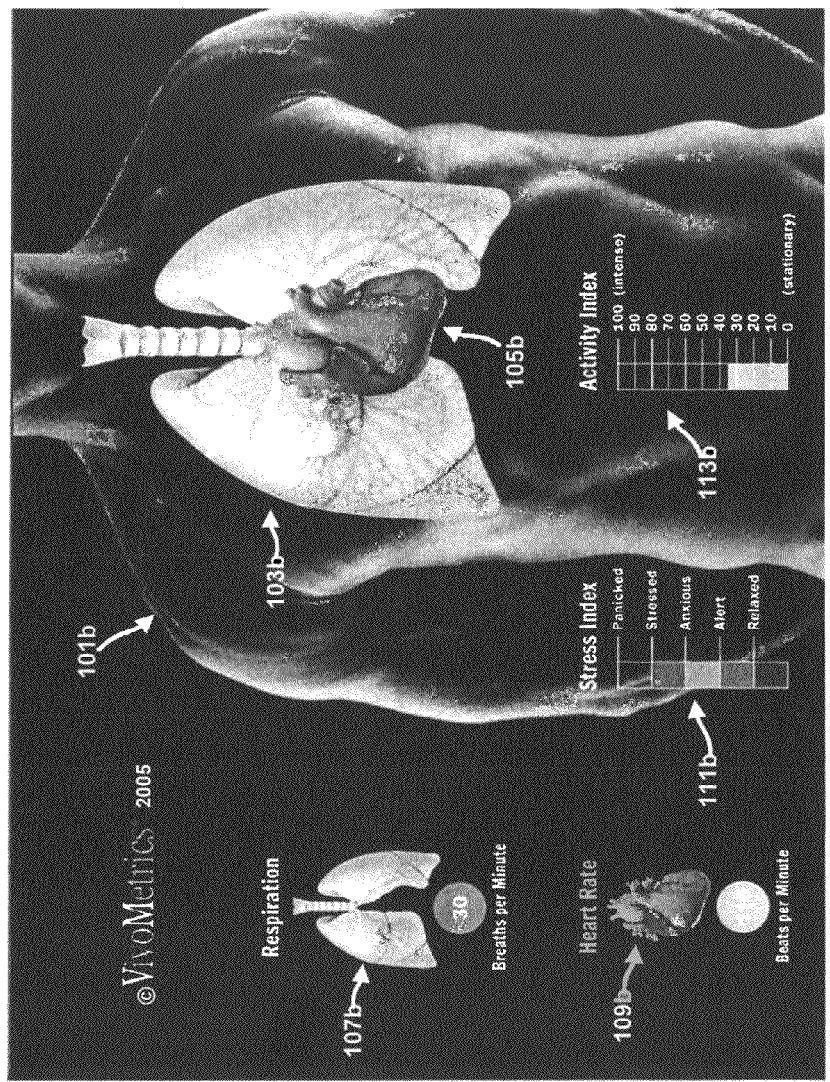

FIGS. 4A-B illustrate a user interface of this invention with several physiologically guided avatars. Although illustrated in black and white, this interface is displayed in color. FIG. 4A illustrates a first frame of this user interface. There are two physiologically-guided avatars: lung avatar 103a guided by a respiration rate, and heart avatar 105a guided by a cardiac rate. During a respiratory cycle from inhalation to exhalation and back to inhalation the lung avatar behaves by expanding, contacting, and then expanding again in synchrony with the monitored inhalation and exhalation. Similarly, during a cardiac cycle from diastole to systole and back to diastole, the heart avatar behaves by expanding, contacting, and then expanding again in synchrony with the heart data. Specifically, FIG. 4A depicts lung avatar 103a as expanded in inhalation, and heart avatar 105a as expanded in diastole.

User interface can optionally include additional display elements. Preferably, the additional elements can provide the context of avatar behaviors. For example, the display background is a substantially uniform color contrasting with the display elements. The heart and lung avatars are displayed as in an image of a torso 101a in order to provide a realistic context. Numeric data elements can also displayed. Here, numeric respiration rate 107a is updated to display the value of the current respiration rate, and the accompanying lung image (avatar) is shaded to reflect the current respiratory rate. Numeric cardiac rate 109a is similarly updated and accompanying static cardiac image (avatar) is similarly shaded.

Also displayed is thermometer display 113a representing a subject's activity index. This index represents the intensity of the monitored subject's physical activity, and can be derived from, e.g., accelerometer data. Further, thermometer-type display 111a represents a subject's presents the value of a stress index, which here is intended to reflect the monitored subject's current state of psychological stress. It can be derived by combining a plurality of physiological monitoring data types. The activity level and the stress displays provide the context for interpreting the cardio-respiratory guided avatars and other display elements.

FIG. 4B (corresponding elements in FIGS. 4A and B have suffices "a" and "b", respectively) illustrates a different frame of the same this user interface. Here, cardiac avatar 105b is illustrated in a contracted, diastolic state; and lung avatar 105b is illustrated in a contracted, exhalation state. Numeric respiration and cardiac data, 107b and 109b, indicate increased cardio-respiratory activity. These increased rates occur in the context of increased physical activity 113b and increased psychological stress 111b.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A system for displaying physiological information of a user comprising:
   a wearable sensor for acquiring real time physiological data of the user including cardiac stroke volume;
   a processor operatively connected to the sensor, the processor adapted to receive the real time physiological data from the sensor; and
   a display for visually presenting an avatar, the avatar including a graphical element representing the real time physiological data of the user,
   wherein the graphical element is a substantially realistic heart image representing the real time cardiac data of the user, wherein the processor dynamically changes a size of at least a portion of the substantially realistic heart image in proportion to the cardiac stroke volume.

2. The system of claim 1, wherein the physiological data includes real time respiratory data.

3. The system of claim 2, wherein the avatar includes a second graphical element representing the real time respiratory data of the user,
wherein the second graphical element expands and contracts in proportion to the real time respiratory data of the user.

4. The system of claim 3, wherein the avatar includes a torso image, and
wherein the graphical element and the second graphical element are displayed in the torso image.

5. The system of claim 1, wherein the display presents a plurality of avatars representing the real time physiological data of multiple users.

6. The system of claim 1, wherein the system further includes a memory device to store the real time physiological data of the user.

7. A method for displaying physiological data of a user during an athletic activity, comprising:
receiving from a wearable sensor real time physiological data of the user including real time respiratory volume during the athletic activity;
displaying on a display a torso image; and
displaying on a display a graphical element corresponding to the real time physiological data in the torso image, wherein the size of at least a portion of the graphical element dynamically changes in proportion to the real time respiratory volume.

8. The method of claim 7, wherein the physiological data includes respiratory data.

9. The method of claim 8, wherein the physiological data includes cardiac data including real time cardiac stroke volume.

10. The method of claim 9, further comprising displaying a second graphical element that is a substantially realistic heart image, wherein the substantially realistic heart image expands and contracts in proportion to the real time cardiac stroke volume.

11. The method of claim 7, wherein the graphical element expands and contracts in proportion to the real time respiratory volume.

12. The method of claim 7, wherein the graphical element represents a lung and wherein the graphical element expands and contracts in proportion to real time respiratory volume.

13. The method of claim 7, wherein the graphical element comprises an avatar including a visual image of the user.

14. The method of claim 7, wherein the wearable sensor and the display are separate devices.

15. The method of claim 7, wherein the sensor and display are part of the same device.

16. A method for displaying physiological data of a user during an athletic activity comprising:
providing a wearable sensor configured to collect real time physiological data of the user including activity data representing the intensity of the athletic activity, respiratory data and cardiac data during the athletic activity;
receiving the real time physiological data;
displaying on a display a first avatar including a first graphical element having an outer border, the first graphical element corresponding to the real time respiratory data;
displaying on a display a second avatar including a second graphical element having an outer border, the second graphical element corresponding to the real time cardiac data; and
displaying on a display a third avatar including a third graphical element corresponding to the real time activity data,
wherein the outer border of at least a portion of the first graphical element dynamically changes in proportion to the real time respiratory data, and
wherein the outer border of at least a portion of the second graphical element dynamically changes in proportion to the real time cardiac data.

17. The method of claim 16, wherein the real time respiratory data is respiratory volume.

18. The method of claim 16, wherein the real-time cardiac data is cardiac stroke volume.

19. The method of claim 16, wherein the outer border of the first graphical element increases and decreases in size in proportion to the real time respiratory data.

20. The method of claim 16, wherein the first graphical element is a lung, and
wherein the first graphical element expands and contracts in proportion to the real time respiratory data of the user.

21. The method of claim 16, wherein the second graphical element is a substantially realistic heart image and wherein the substantially realistic heart image expands and contracts in proportion to the real time cardiac data of the user.

22. The method of claim 16, wherein the wearable sensor and the display are separate devices.

23. The method of claim 16, wherein the sensor and display are part of the same device.

24. The method of claim 16, further comprising displaying multiple avatars corresponding to real time physiological data of multiple users.

25. The method of claim 16, further comprising displaying on a display a fourth avatar including a fourth graphical element corresponding to real time psychological stress of the user.

* * * * *